United States Patent [19]

Farrar et al.

[11] Patent Number: 4,820,872
[45] Date of Patent: Apr. 11, 1989

[54] PROCESS FOR HYDROLYZING NITRILES

[75] Inventors: David Farrar; Peter Flesher; Gerald Benn, all of West Yorkshire, England

[73] Assignee: Allied Colloids Ltd., Great Britain

[21] Appl. No.: 852,250

[22] PCT Filed: Jul. 16, 1985

[86] PCT No.: PCT/GB85/00320
§ 371 Date: Mar. 6, 1986
§ 102(e) Date: Mar. 6, 1986

[87] PCT Pub. No.: WO86/00614
PCT Pub. Date: Jan. 30, 1986

Related U.S. Application Data

[63] Continuation-in-part of Ser. No. 437,385, Oct. 28, 1982, Pat. No. 4,543,423.

[30] Foreign Application Priority Data

Jul. 17, 1984 [GB] United Kingdom ................. 8418136
Sep. 7, 1984 [GB] United Kingdom ................. 8422640
Dec. 12, 1984 [GB] United Kingdom ................. 8431292

[51] Int. Cl.$^4$ ............................................ C07C 102/08
[52] U.S. Cl. ................................... 564/128; 564/124; 564/126; 564/127
[58] Field of Search ................................. 564/127, 128

[56] References Cited

U.S. PATENT DOCUMENTS

| | | | |
|---|---|---|---|
| 3,642,643 | 2/1972 | Habermann | 564/127 X |
| 3,670,020 | 6/1972 | Moore | 564/160 X |
| 3,804,897 | 4/1974 | Haefele et al. | 564/128 |
| 3,911,009 | 10/1975 | Yoshimura | 564/127 |
| 4,056,565 | 11/1977 | Matsuda | 564/127 |
| 4,365,091 | 12/1982 | Masaaki et al. | 564/128 X |
| 4,543,423 | 9/1985 | Farrar et al. | 564/127 X |

OTHER PUBLICATIONS

"The Influence Of The pH Of An Aqueous Solution Of Acrylonitrile..." by I. O. Mikhailishin et al. Chemical Technology, 1983 No. 3, The Lvov Polytechnic Institute.

Primary Examiner—Robert V. Hines
Attorney, Agent, or Firm—Ostrolenk, Faber, Gerb & Soffen

[57] ABSTRACT

When making an unsaturated amide by hydrolysis of an unsaturated nitrile in the presence of a catalyst such as Raney copper and an oxidizing agent such as copper nitrate, by-product formation is reduced by including a reagent selected from reducing agents and acids that are substantially non-oxidizing relative to the said oxidizing agent. The preferred reagents are acidic buffers, especially acetic acid and copper acetate. Washing with such a buffer a Raney catalyst or other catalyst that is to be used for catalyzing the hydrolysis of an unsaturated nitrile to an unsaturated amide reduces the temperature surge that otherwise occurs upon addition of the catalyst to the reaction mixture.

27 Claims, No Drawings

PROCESS FOR HYDROLYZING NITRILES

This United States of America application is a continuation in part of U.S. Ser. No. 437,385 filed Oct. 28th 1982 now U.S. Pat. No. 4,543,423, corresponding to EP No. 78178.

It is known to make amides of the formula $RCONH_2$ where R is a hydrocarbon group having 1 to 10 carbon atoms by hydrolysis of the corresponding nitrile RCN by water in the presence of a solid catalyst. A wide range of catalysts have been proposed and are reviewed in, for instance, U.S. patent specification 3,997,606. However most recent literature concentrates on the use of copper as the catalyst, usually Raney copper.

The emphasis throughout the literature is on providing a catalyst having the maximum activity, so as to achieve the highest rate of conversion from nitrile to amide.

It is well established in the literature that it is desirable to include activators to improve the activity of the catalyst. For instance U.S. Pat. No. 3,381,034 descrives the use of a mixture of zero valent, monovalent and divalent copper, the ionic copper being introduced as cupric chloride, sulphate or cyanide and two examples show the use of acetic acid with cuprous chloride.

In U.S. patent specification 3,911,009, the use of Raney or other suitable copper in combination with dissolved promoters selected from copper sulphate, copper nitrate, copper chloride and copper salts of lower fatty acids was described. Copper nitrate was shown to be a very active activator and copper acetate was shown to be less effective.

In European Patent Specification No. 78178, we described how the activity of the Raney copper could be improved by partially oxidising it, before utilisation in the reactor, by contact with oxygen, peroxide, iodate, chlorate, bromate or nitrate, the hydrolysis of the nitrile preferably being conducted in the presence of a copper nitrate or other suitable promoter for increasing activity.

Various other processes have been described. For instance in European Patent Specification No. 37178 activity of a copper catalyst is maintained by electrolysis under conditions such that the catalyst has from 0.75 to 12.5 monolayers of ionic copper on its surface. It is shown in the specification that the activity of the catalyst decreases at lesser or higher amounts of ionic copper.

It is recognised in the literature that the catalyst becomes deactivated during prolonged use and that this deactivation can be due to oxidation. See for instance U.S. patent specification No. 3,886,213. It is also recognised that deactivated catalyst can be regenerated. For instance in U.S. patent specification No. 3,642,894 deactivated catalyst is oxidised and then reduced.

It has been thought to be satisfactory to conduct the hydrolysis in the presence of deactivated catalyst provided that fresh, active, catalyst is also present. Thus fresh, active Raney or other copper catalyst may be charged continuously or intermittently to the reactor over a prolonged period and water, acrylonitrile and any dissolved promoter (for instance copper nitrate) may be charged continuously. Acrylamide is removed continuously. All or some of the catalyst may remain in the reactor. Typically the process is conducted until the amount of used or "stale" catalyst in the reactor is so high that it is necessary to terminate the reaction, discharge the used catalyst from the reactor, and restart the process.

Many of the hydrolysis processes are exemplified in the literature as being conducted at, for instance, 70° C. but of course the hydrolysis proceeds faster at higher temperatures and in U.S. 3,911,009 temperatures up to 150° C. are proposed and in U.S. 3,381,034 a temperature of 125° C. is exemplified.

Although the known processes can give good conversions, a problem that has been encountered is that during a prolonged run the formation of by-products tends to increase. For instance when starting from acrylonitrile, the formation of ethylene cyanohydrin and $\beta$-hydroxy propionamide starts to increase after prolonged operation. Removal of these impurities from the end product is inconvenient. Their origin has not been clear and so, as soon as a reactor started producing unacceptable quantities of by-products, it has been necessary to close down the reactor, empty it, and recharge it.

This problem of by-product formation, or lack of selectivity of the catalyst, is a particular problem when the process is performed under conditions of high catalyst activity, especially at elevated temperatures, typically above 110° C. At these higher temperatures the catalyst is more active, and thus effects faster hydrolysis, but is less selective, and thus causes more by-product formation, than at lower temperatures.

At present it is often considered that the most reliable way of obtaining high purity is by an enzymatic process, but such processes are inconvenient to operate.

In Chemical Abstracts Volume 99 No. 22951g, the selectivity of a reduced copper oxide catalyst is increased by treating the catalyst before use with sulphuric acid or acrylic acid.

In processes utilising Raney copper as the catalyst, the copper is conventionally made by treatment of a copper alloy with lkali and then washing the catalyst with water to remove free alkali from the catalyst.

The present state of the art therefore is that numerous proposals have been made as to how to prepare a catalyst for use in the hydrolysis of nitrile to amide and how to conduct the hydrolysis, with the intention of improving activity, but in practice increasing the activity, especially when operating at temperatures above 110° C., is always accompanied by increased formation of by-products. It would be very desirable to be able to achieve satisfactory activity with decreased by-product formation.

In the invention, an amide of the formula $RCONH_2$, where R is an ethylenically unsaturated hydrocarbon group of 2 to 10 carbon atoms, is made by hydrolysis of the corresponding nitrile RCN in a reaction mixture comprising a solid catalyst for the hydrolysis reaction, water, an oxidising agent that increases the activity of the catalyst by forming oxidised, catalytically active, sites on the catalyst and a polymerisation inhibitor, and by-product formation is reduced by including in the reaction mixture a reagent that destroys some, but not all, of the oxidised sites. Thus the water includes a dissolved oxidising agent (which may be gaseous oxygen) and a dissolved reagent to destroy some but not all of the oxidised sites.

We believe that good catalytic activity in the process necessitates the presence on the catalyst of a significant number of catalytically active sites but that if there are too many catalytically active sites on the catalyst, its tendency to form by-products increases. Thus, there should not be a continuous layer of active sites over the catalyst. We believe the active sites to be oxidised, anionic salts. Prior to the present invention "over oxidised" catalyst was thought merely to be of low activity so that it was harmless to leave this material in the reactor as a relatively inert material provided fresh catalyst was charged to the reactor. We now realise this "over oxidised" catalyst is not inert but instead promotes the formation of by-products. Accordingly in the invention, sites are formed during the process by oxidation and some of the formed sites are destroyed so as to keep the number of sites at a level below that at which by-product formation becomes significant.

It is necessary both to form the sites and to destroy the sites, rather than merely forming the desired number of sites without subsequent destruction of them, because site formation will inevitably continue throughout the process and so, unless sites are destroyed, it is inevitable that in a prolonged batch or continuous process the number of sites on the catalytic surface will increase continuously.

The optimum degree of oxidation of the catalyst, and thus the relative proportions of the oxidising agent and the reagent for destroying the sites, can be determined by operating the process initially with the oxidising agent in the absence of the destroying reagent until optimum conversion is achieved and running the process at this level until by-product formation starts significantly, whereupon destroying reagent is added at low, but gradually increasing, levels until by-product formation drops and activity is substantially maintained.

The reagent for destroying the sites is preferably a reducing agent or an acid (or a non-interfering salt thereof) that is non-oxidising relative to the said oxidising agent. It is water soluble.

Irrespective of the precise mechanism by which the invention operates, according to a second aspect of the invention a process for making an amide of the formula RCONH$_2$, where R is as defined above, by hydrolysis of the corresponding nitrile RCN in a reaction mixture comprising a solid catalyst for the hydrolysis reaction, water, and oxidising agent that increases the activity of the catalyst by forming oxidised, catalytically active, sites on the catalyst and a polymerisation inhibitor is characterised in that by-product formation is reduced by including in the reaction mixture a reagent selected from reducing agents and acids, and non-interfering salts thereof, that are non-oxidising relative to the said oxidising agent, the amount of the said reagent being sufficient to reduce by-product formation but insufficient to reduce substantially the formation of the amide.

The process of the invention is preferably conducted in the presence of freshly charged, active, catalyst and catalyst that has become de-activated by residence in the reaction mixture. Thus a preferred way of conducting the process comprises feeding water, the catalyst, the oxidising agent, the nitrile and the specified reagent to a reaction vessel substantially continuously, removing the resultant amide from the vessel substantially continuously, and allowing the amount of solid catalyst in the vessel to increase significantly during the process and then discharging the catalyst from the vessel. Thus the components of the reaction mixture may be fed in a truly continuous or intermittent manner into the vessel, either individually or in combination and the product of the reaction may be removed in a truly continuous or intermittent manner from the vessel. However the catalyst is either not removed from the vessel for prolonged periods, or is removed at a rate less than the rate at which it is introduced, as a result of which the amount of catalyst in the vessel will increase significantly during the process, for instance it will more than double in weight between start up of the process and final discharge of the catalyst. Typically the process is conducted until the reaction vessel is so full of catalyst that there is inadequate volume for liquid phase, whereupon the catalyst is discharged from the vessel.

The reaction temperature in the vessel is preferably between 100° and 150° C., most preferably 110° to 130° C. Even though reagent to destroy sites is included in the reaction mixture, the overall activity of the catalyst can be increased in the invention and optimum results are obtainable at a temperature that may be 5° to 15° C. less than is the optimum in the absence of the said reagent. Best results are generally obtained at temperatures of from 115° to 125° C., preferably about 120° C.

The hydrocarbon group R preferably is an olefinic group having 2 to 8 carbon atoms. The invention is of most value applied to the production of acrylamide or methacrylamide from acrylonitrile of methacrylonitrile.

The solid catalyst can be selected from amongst any of the solid catalysts suitable for use in the hydrolysis in the presence of an oxidising agent, for instance as discussed in U.S. patent specification No. 3,997,606. Preferably the catalyst is a copper containing catalyst. Best results are achieved with a substantially black copper catalyst since it seems that red, pink or salmon coloured copper does not serve as a catalyst in the invention. It may however serve as a raw material from which black copper catalyst can be made, for instance by oxidation during the process. Thus the reactor could be charged with salmon, red or pink coloured powdered copper and this could be oxidised to a black state in the reactor, generally before passage of the nitrile through the reactor.

The catalyst may be a true black colour or, for instance purple to black, but it must not be pink, red or salmon coloured.

Suitable black copper catalysts are described in U.S. Pat. No. 4,169,107. The black copper catalyst can be made by reduction of copper oxide but generally is Ullmann copper or, preferably, Raney copper. The precise chemical state of such black copper catalysts is uncertain but they probably consist of metallic copper carrying a partially oxidised surface layer. The catalyst preferably has a very large surface area, as is typical of, for instance, Raney copper.

The black copper catalyst can be introduced into the reactor in a partially oxidised state such that it has optimum activity from the start of the process. For instance Raney copper may be partially preoxidised with a controlled oxidising system comprising oxygen, peroxide, iodate, chlorate, bromate, nitrate or other suitable oxidising agent, for instance as described in EP 78178. It may then not be essential to make deliberate addition of oxidising agent to the water used for hydrolysis of the nitrile to the amide but in practice this water will contain some oxidising agent as a result of having dissolved oxygen in it (unless extreme precautions have been taken) and so even when no deliberate addition of oxidising agent is made, it is still valuable to operate the process using a weak reducing agent or acidic buffer in order to compensate for the otherwise inevitable gradual oxidation of the already oxidised catalyst. Generally however deliberate addition of oxidising agent is made to the reaction water in which event the catalyst can be introduced in partially preoxidised form, as discussed above, or can be introduced as, for instance, Raney copper, Ullmann copper or reduced copper oxide.

The oxidising agent may be oxygen dissolved in the reaction water (and which may be present as an incidental impurity or may have been deliberately metered into the water), iodate, chlorate, bromate, nitrite or nitrate. Very strong oxidising agents such as permanganate and dichromate are generally unsatisfactory as they oxidise the catalyst so fast that it is difficult to control by-product formation. Oxidising agents which generate free radicals, such as peroxide, persulphate and perborate, are generally unsatisfactory because of the risk of causing polymerisation of the unsaturated amide. The preferred oxidising agent is nitrate.

This, and other oxidising anions, may be introduced in any convenient form, for instance as a salt with sodium, potassium, lithium, zinc or, preferably aluminium or copper. The use of copper salts, such as copper nitrate, is particularly preferred as the introduction of copper nitrate generates, in the solution, dissolved monovalent copper and this serves as polymerisation inhibitor. If necessary, additional monovalent copper or other conventional polymerisation inhibitor may be added to prevent polymerisation of unsaturated material during the process or, especially, during the working up of the product of the process.

A suitable weak reducing agent that can be added to prevent by-production formation is sodium borohydride. Preferably however the reagent that is added is an acidic buffer. Preferred acidic buffers are water soluble non-polymerisable organic carboxylic acid as free acid or salt, especially aliphatic mono-carboxylic acids containing 2 to 8 carbon atoms, acetic acid being especially preferred. Polymerisable carboxylic acids, such as acrylic acid, are less suitable because of the risk that they will react within the reaction mixture to form different by-products. Instead of using a non-polymerisable aliphatic mono-carboxylic acid, other organic acid buffers that may be used include dicarboxylic acids such as succinic acid and aromatic acids such as benzoic acid and amino benzoic acid. Preferably the dissociation constant $pK_{a1}$ of the acid is between 2 and 7, most preferably 4 to 6. The acidic buffer may be introduced in the form of a free acid or a water soluble salt, preferably with a weak base.

If the acidic buffer is introduced as a salt, the cation of the salt must not interfere with the hydrolysis or with the subsequent use of the amide formed by the hydrolysis. Many metallic cations are therefore best avoided. Alkali metals, such as sodium, can sometimes be used but if the end product is purified by ion exchange the presence of these or other unwanted cations may provide an undesirable load on the ion exchangers. Preferably the acidic buffer is introduced as the free acid (for instance acetic acid) or as the copper salt, for instance copper acetate but other salts that can be used include the aluminium and sodium salts, for instance sodium acetate.

The acidic buffer or weak reducing agent may be added throughout the process, including from start up, or may be added only after a prolonged time, for instance when by-product starts to be formed. Once addition is made, it may be continuous or intermittent or it may be sufficient merely to add the weak reducing agent or acidic buffer for a short while and then to continue the process without further addition of weak reducing agent or acidic buffer until by-product formation resumes. We have surprisingly observed that, once acidic buffer or reducing agent has been added to the reactor, there may be less tendency for subsequently added catalyst to move to a state at which by-product formation becomes serious.

In the preferred process, using copper nitrate and acetic or other carboxylic acid (often as copper salt), the preferred molar ratio copper nitrate:acetate is from 2:1 to 1:50, preferably 1:5 to 1:30, when the acetate is being added continuously. If it is being added discontinuously the amount is typically 100 to 1000 ppm, preferably 300 to 600 ppm.

The concentration of copper in solution in the reactor is generally 10 to 1000 ppm, preferably 50 to 500 ppm. The concentrations of oxidising agent and buffer/reducing agent (when present) are each generally 10 to 5000, preferably 100 to 1000 ppm.

If a strong acid, or a salt thereof, or reducing agent is being used instead of the acetic acid or other weak reducing agent or acidic buffer, then the amount will generally be near the bottom of or below these ranges since higher amounts may totally deactivate the catalyst. For instance when using black Raney copper it is essential that the amount is not sufficient to significantly convert the catalyst to a pink, red or salmon state since if this conversion does occur there will be inadequate activity for the hydrolysis of the nitrile to the amide. Thus the combination of the strength of the reducing agent or acidic material and the amount of the reducing agent or acidic material must be such that the desired byproduct formation is achieved without substantial and unacceptable reduction in the formation of amide.

If strong acids are used, in carefully controlled amounts, they must be non-oxidising relative to the said oxidising agent. Thus their anions must either be non-oxidising or must oxidise the catalyst less strongly than the described oxidising agent, in order that they should be capable of controlling the effect caused by over oxidation of the catalyst. The acidic material may be a free acid, for instance hydrochloric acid, hydrofluoric acid, sulphuric acid, phosphoric acid, phosphorus acid, sulphurous acid or sulphonic or sulphamic acids, including for instance acrylamido methyl propane sulphonic acid, trichloroacetic acid, or salts of these with weak bases, for instance salts with copper, aluminium or zinc, for instance cupric sulphate or cupric chloride. Salts of strong acids with strong bases are unsatisfactory.

The amounts of these strong acids, and salts of strong acids, must be very low. For instance the molar ratio of copper nitrate or other oxidising anion to the anion of the strong acid is below 1:1. If the ratio is as high as, for instance, 1:2 for a prolonged period, it will result in the black copper catalyst being converted to a less active pink, salmon or red form, and so is undesirable. Even with the specified very low molar amounts of the strong acids it is difficult to avoid de-activation of the catalyst if the acid is added continuously and so if strong acid is to be used, it is preferably added discontinuously, and preferably once only, during an entire process. For instance if it is found that the by-product formation in any particular process is gradually increasing, a single addition of a small amount of one of the strong acids, or strong acid salts, may be made to reduce or eliminate the tendency for by-product formation. This restoration of the selectivity of the catalyst may be conducted in the reaction mixture or the catalyst may be removed from the reaction mixture and treated with the strong acid, or with the preferred reducing agents or acidic buffers, to restore selectivity, and then re-introduced into a reaction mixture. For instance the addition of strong acid may be continued for the time required for the passage of 0.2 to 2, preferably about 1 volume, of the liquid reaction mixture per volume of reactor vessel.

The catalyst that is introduced into the reaction mixture is preferably a substantially black copper catalyst that has been washed possibly with a reducing agent or strong acid or acid salt, as discussed above, but preferably with an aqueous solution of an acidic buffer, or a salt thereof, as discussed above. The catalyst that is washed, prior to introduction into the reaction mixture or may be unused Raney or other black copper catalyst or may be catalyst that has become non-selective as a result of use as the catalyst in a process for hydrolysing nitrile to amide, with or without feed of oxidising agent to the reaction mixture.

The invention also includes a process in which an amide of the specified formula is made by hydrolysis of the corresponding nitrile in a reaction mixture comprising the nitrile, water and Raney catalyst, preferably Raney copper catalyst, wherein the Raney catalyst is, before incorporation into the reaction mixture, washed with an aqueous solution of an acidic buffer that is a non-polymerisable organic carboxylic aicd, or a salt thereof. This buffer is preferably an aliphatic mono carboxylic acid, generally acetic acid or copper acetate, and preferably has pKa from 2 to 7, preferably 4 to 6. The Raney catalyst that is subjected to this washing will generally have been made by conventional methods, for instance leaching an alkali soluble metal with alkali, such as sodium hydroxide, out of an alloy of the alkali soluble metal with another metal, generally copper, iron or nickel, followed by water washing to a substantially constant pH, generally in the range 7.5 to 10. It appears that, despite the conventional water washing having been conducted to a substantially constant pH, the catalyst may include unwanted basic sites in its structure, possibly due to residual basic material left from the leaching process.

This washing process has the advantage that it eliminates a problem that regularly occurs with hydrolysis processes conducted in the presence of a Raney catalyst, namely that when the fresh catalyst is added to the reaction mixture the addition is always accompanied by an exotherm. Thus if the reaction is being conducted at a steady temperature this temperature will rise when fresh catalyst is added and will eventually drop back to the chosen steady temperature. This temperature surge is undesirable, and may promote by-product formation, but has been accepted as inevitable. The washing process of the invention reduces or eliminates the temperature surge. It appears that the washing with the acidic buffer not only neutralizes residual alkali which remains despite conventional prolonged washing with water, but also de-activates excess active sites from the catalyst.

The washing of the Raney catalyst with the acidic material is generally conducted using an aqueous wash liquor having pH from 2 to 7, preferably from 3 to 7. Preferably the catalyst is stirred with the wash liquor until the liquor acquires a substantially steady pH in the range 3 to 7.5, preferably below 7, eg 5 to 7. Preferably the contact is maintained until the pH is constant.

If the acidic material is a buffer or weak acid then the duration of washing and the concentration of acid may be relatively unimportant, the concentration of acid typically being 0.001 to 10%, preferably 0.01 to 1%, by weight in the aqueous wash liquor. However, if a stronger acid is being used it may be necessary to have very dilute concentrations of the acid, for instance below 100 ppm, typically 5 to 50 ppm. If the concentration is too high, or the duration is too long, the activity of the catalyst in the subsequent hydrolysis or other process may be reduced significantly.

The washing treatment may be applied to commercial Raney catalyst before charging the catalyst into the hydrolysis or other reaction mixture or it may be applied as a final step in the production of a Raney catalyst, that may then be used on site or transported elsewhere. The acid washing generally follows a water wash. The catalyst may be subjected to partial oxidation after the acid washing and before use in the hydrolysis process, generally as described in our European Patent Publication 78178.

In a typical process, an alloy of copper and aluminium is leached with sodium hydroxide at around 50° C. and is aged in solution in conventional manner to give particulate Raney copper. This is then rinsed with water to a constant pH in the range 8 to 11.5 and is then washed with acid in accordance with the invention.

Instead of starting with a copper aluminium alloy, copper alloys with, for instance, magnesium or zinc can be used, in conventional manner. By appropriate choice of the alloy other Raney metals can be made, for instance Raney nickel or Raney iron, in conventional manner.

The catalyst is preferably provided in a particulate form, generally as an aqueous slurry and is charged to a hydrolysis or other reaction mixture whilst the hydrolysis process is being conducted at a desired, generally elevated and controlled, temperature. Also the catalyst can be used for initial start-up of the process. Charging of the catalyst to the reaction mixture may be continuous or intermittent.

The hydrolysis process may be conducted in the absence of any dissolved activator, for instance as described in U.S. Pat. No. 3,894,084, or may be conducted in the presence of dissolved activator, for instance as described in U.S. Pat. No. 3,911,009.

The processes of the invention in which the hydrolysis is conducted in the presence of reducing agent, buffer or other said reagent can very conveniently be conducted by charging a reactor with catalyst, feeding water, nitrile and nitrate or other oxidising agent to the reactor, continuously removing amide from the reactor, feeding water reducing agent or acidic buffer when necessary to the reactor and discharging the reactor when activity finally drops and/or when the reactor is full of spent catalyst and/or when by-product formation becomes serious. This discharge generally is not required until at least 4 weeks and often 8, 12 or 16 weeks or more after start up, whereas prior to the invention it would generally have been required within 2 or 3 weeks from start up if the process temperature is 120° to 130° C.

The duration of the process before having to discharge the catalyst can be extended by adding a small amount of the strongly acidic material for a short period when necessary to restore the catalyst to a state in which it gives substantially no byproduct. Thus a preferred process has continuous addition of copper nitrate, continuous or intermittent addition of acidic buffer such as copper acetate or acetic acid, and infrequent addition of a small amount of strongly acid material, e.g., $CuCl_2$.

The process of the invention has considerable advantages compared to processes conducted under conditions that are substantially the same except for the addition of acetate or other acidic material or reducing agent.

One advantage is that the resultant amide can be of higher quality and can have lower degrees of contamination. When the amide is a polymerisable amide such as acrylamide, this can be manifested by the fact that polymerisation under standard conditions will lead to a higher intrinsic viscosity for the polymer.

Another advantage is reduced production of specific by-products such as ethylene cyanohydrin. These reductions in by-product formation are of particular value in large scale commercial processes designed to give high rates of amide production since, before the invention, increasing the rate of amide formation has tended to be accompanied by increased by-product formation.

Another advantage is that the process is much more accurately reproducable from one run to the next.

Another advantage is that the invention reduces the consumption of solid catalyst. For instance the amount of Raney copper required in a process of the invention using nitrate and acetate may be less than 75%, for instance 66%, the amount required when using nitrate alone.

Another advantage is that the process can be operated at temperatures 5° to 15° C. lower than without the addition of the specified reagent without loss of selectivity or activity.

The following are examples of the invention.

Example 1 shows a suitable method of preparing a Raney catalyst for a hydrolysis reaction, Examples 2 and 3 illustrate hydrolysis processes conducted using addition of a suitable reagent, Example 4 demonstrates, in a laboratory process, that the disadvantages of an over-oxidised copper catalyst can be overcome by adding stronger acids or acid salts, and Example 5 illustrates the advantages of the process in commercial practice.

EXAMPLE 1

A Raney catalyst may be made in conventional manner by leaching aluminum from an alloy of copper and aluminum using sodium hydroxide followed by prolonged washing with deoxygenated water until the resultant slurry, on standing, has a pH of about 11.

Part of this water washed catalyst is then subjected to prolonged washing with aqueous acetic acid until the resultant slurry, on standing, has a substantially constant pH of about 5.5.

Acrylamide is made continuously in a sealed reactor having a temperature of about 125° C. and having a liquid charge consisting of about 30% acrylamide, 10% acrylonitrile and 60% water and containing about 250 ppm dissolved copper, the reactor also being filled to about one-quarter of its volume by particulate copper, this being a blend of active Raney copper and used copper catalyst.

Acrylonitrile, water and dissolved copper are supplied substantially continuously, the contents are stirred substantially continuously and acrylamide can be removed from the reactor by a draught tube, all in conventional manner.

When it is necessary to replenish the Raney copper in the reactor, one kilo (dry weight) of the water washed or acid washed slurries are added to the reactor per 20 kilos used copper in the reactor.

When the catalyst that is added is the water washed catalyst, it is observed that the temperature in the reactor rises temporarily to about 140° to 145° C., before dropping again to the chosen value of about 125° C. and the production of impurities such as ethylene cyanohydrin and beta-hydroxypropionamide increases temporarily before dropping back to its previous level. However when the acid washed catalyst is added there is substantially no increase in temperature or impurity production.

EXAMPLE 2

A stirred closed reactor was charged with Raney copper (to fill about 5% by volume of the reactor) and a feed of 42.5% acrylonitrile and 57.5% water was passed through the reactor at about 125° C. whilst stirring. The overflow from the reactor consisted of approximately 30% acrylamide, 20% acrylonitrile and 50% water and acrylamide was worked up from this in conventional manner.

The water charged to the reactor contained dissolved copper salt in an amount such that the concentration of dissolved copper in the overflow was held at about 250 ppm.

An initial start up the water feed contained copper nitrate as the added copper salt and within a few hours the reactor was operating satisfactorily. The concentration of ethylene cyanohydrin was about 0.1% based on acrylamide. After about 8 days operation the concentration of ethylene cyanohydrin increased up to about 0.6%, based on acrylamide. The copper nitrate feed was replaced entirely by copper acetate for the time necessary for the reactor to be charged with copper acetate at the same copper ion concentration as when it has been charged with copper nitrate, and then the copper nitrate feed was resumed. The concentration of ethylene cyanohydrin dropped to 0.10% of acrylamide. The rate of production of acrylamide was substantially unchanged.

Raney copper was, throughout the process, charged into the reactor as necessary. The concentration of ethylene cyanohydrin remained substantially constant in the range 0.10 to 0.2% based on acrylamide for 48 days whereupon it started increasing again and so the copper nitrate feed was replaced by copper acetate, as before. Again the ethylene cyanohydrin concentration dropped while the overall rate of production of acrylamide stayed substantially constant.

EXAMPLE 3

Using the same reactor system and reactant feed as Example 1, the experiment was repeated but using a continuous acetic acid feed. Cu(NO$_3$) was continually added to the reactor as in Example 1 for a period of 12 hours and a consistent rate of acrylamide product established. The ethylene cyanohydrin concentration at this time was 0.32% on acrylamide. Acetic acid was then fed continually to the reactor in the molar ratio of 3/1 acetic to Cu(NO$_3$)$_2$. After five days the ethylene cyanohydrin had risen to 0.45% and the beta-hydroxy propionamide to 0.23% on acrylamide. No change in the rate of acrylamide production was observed.

The addition of Raney copper catalyst was stopped after seven days and the acrylamide production rate fell to 55% the initial value; after nine days and the ethylene cyanohydrin and beta-hydroxy propionamide concentrations rose to 1.1% and 0.5% respectively. The rate of acetic acid addition was doubled to give a 6/1 molar ratio acid:Cu$^{2+}$.

After ten days the ethylene cyanohydrin and beta-hydroxy propionamide concentrations had fallen to 0.9 and 0.35% respectively and the catalyst addition restarted. By day thirteen the acrylamide rate had increased to its initial value and the two impurity concentrations were 0.39 and 0.225% respectively.

EXAMPLE 4

To demonstrate the effect of adding a strongly acidic material to a catalyst that is so highly oxidised that byproduct formation occurs, a highly oxidised catalyst was formed and then was used, in the absence of additional deliberate oxidation, in the presence of various additions of copper chloride, hydrochloric acid, sodium chloride, copper sulphate, sulphuric acid and sodium sulphate. This is a short term laboratory process and an equivalent commercial process it would be necessary to add copper nitrate or other oxidising agent during a prolonged process.

In this example a sample of Raney copper was pretreated with 200 ppm (on Raney copper) Cu$^{2+}$, as the nitrate salt, for 18 hours at 60° C. The catalyst was then washed with deoxygenated water to remove any soluble ions. This material was then compared with the washed untreated copper as a catalyst for the hydration of acrylonitrile to acrylamide as follows.

0.15 g copper catalyst, 3.15 g deoxygenated water and 2 cm$^3$ deoxygenated acrylonitrile were placed in a glass test tube, cooled in liquid nitrogen and the tubes sealed. The tubes and their contents were heated to 130° C. for 3 hours in an oilbath. The tubes were then cooled to room temperature, opened and the extent of conversion of the contents analysed by GLC. The results are shown in Table I.

TABLE I

| Sample | % ACM | % ECH | % BHP | % DCDEE |
|---|---|---|---|---|
| (1) Raney copper | 40.2 | 0.11 | 0.13 | 0.0077 |
| (2) Raney copper Cu(NO$_3$)$_2$ pretreated | 43.5 | 0.20 | 0.21 | 0.0138 |

The results show that pretreating the copper catalyst with copper (II) nitrate has increased the yield of acrylamide but also significantly increased the levels of impurities.

This overoxidised catalyst was then used in three separate tests. In one, various amounts of copper chloride, hydrochloric acid or sodium chloride were added. In another, very small amounts of copper chloride were added and in the third, various amounts of copper sulphate, sulphuric acid and sodium sulphate were added.

The results are shown in tables II, III and IV.

TABLE II

| Sample | | % | % | % | % |
|---|---|---|---|---|---|
| ppm Cu$^{2+}$ | ppm Cl$^-$ | ACM | ECH | BHP | DCDEE |
| (3) 100 | 112 | 44.3 | 0.048 | 0.07 | |
| (4) 200 | 224 | 35.3 | 0.044 | 0.03 | |
| (5) 500 | 560 | 24.4 | 0.11 | 0.02 | |
| (6) — | 112 (as HCl) | 40.2 | 0.14 | 0.13 | 0.0031 |
| (7) — | 112 (as NaCl) | 43.2 | 0.15 | 0.22 | 0.0077 |

TABLE III

| Pretreated catalyst | | % ACM | % ECH | % BHP | % DCDEE |
|---|---|---|---|---|---|
| | | 39.8 | 0.17 | 0.20 | 0.013 |
| 1 ppm Cu$^{2+}$ | 1.12 ppm Cl$^-$ | 44.9 | 0.16 | 0.17 | 0.010 |
| 5 ppm Cu$^{2+}$ | 5.6 ppm Cl$^-$ | 43.2 | 0.14 | 0.16 | 0.009 |
| 10 ppm Cu$^{2+}$ | 11.2 ppm Cl$^-$ | 42.5 | 0.13 | 0.16 | 0.007 |
| 50 ppm Cu$^{2+}$ | 56 ppm Cl$^-$ | 49.2 | 0.11 | 0.15 | 0.004 |

TABLE IV

| Pretreated catalyst | | % ACM | % ECH | % BHPA | % DCDEE |
|---|---|---|---|---|---|
| | | 38.4 | 0.167 | 0.183 | 0.008 |
| 100 ppm Cu$^{2+}$ | 151 ppm SO$_4^{2-}$ | 41.1 | 0.0101 | 0.097 | 0.0028 |
| 200 ppm Cu | 302 ppm SO$_4^{2-}$ | 30.8 | 0.117 | 0.040 | 0.0014 |
| 500 ppm Cu | 755 ppm SO$_4^{2-}$ | 0.6 | — | 0.040 | — |
| — | 151 ppm SO$_4^{2-}$ (as H$_2$SO$_4$) | 39.9 | 0.078 | 0.086 | 0.0014 |
| — | 151 ppm SO$_4^{2-}$ (as Na$_2$SO$_4$) | 39.6 | 0.365 | 0.312 | 0.0365 |

These results show that the use of low amounts of copper chloride reduce the formation of impurities without reducing acrylamide formation and that very low amounts, when starting from an overoxidised catalyst, can even give an increase in the amount of acrylamide formation as well as a reduction in impurity formation. They show that hydrochloric acid can give some reduction in byproduct formation but that sodium chloride is of little effect. They show that increasing the amount of copper chloride reduces the level of impurities but also reduces the amount of acrylamide that is formed. The results also show similar effects for copper sulphate and sulphuric acid but that salts of strong acids with strong bases (sodium sulphate) give a marked deterioration.

EXAMPLE 5

A stirred closed reactor was filled to about 5% by volume with Raney copper that had been washed with aqueous acetic acid and a feed of 42.5% acrylonitrile and 57.5% water. Raney copper was added during the process. The water from start up included copper nitrate and acetic acid in a molar ratio of 1:2. During the first three weeks of the run the ethylene cyanohydrin content varied between about 0.06 and 0.14%. The acetic acid quantity was then increased so that the molar ratio copper nitrate:acetic acid was then 1:18 and the temperature reduced to about 120° C. The ethylene cyanohydrin content then remained at a level of from 0.02 to 0.05% for a further three weeks. The percentage yield of acrylamide was 99.8% based on acrylonitrile.

We claim:

1. In a process for making an amide of formula NCONH$_2$ where R is an ethylenically unsaturated hydrocarbon group of 2 to 10 carbon atoms by hydrolysis of the corresponding nitrile RCN in a reaction mixture comprising a solid, substantially black, copper catalyst for the hydrolysis reaction, water an oxidizing agent that is selected from oxygen metered into the reaction mixture, iodate, chlorate, bromate, nitrate and nitrate that that increases the activity of the catalyst for the formation of the amide and of by-products by forming oxidised, catalytically active, sites on the catalysts and a polymerisation inhibitor for inhibiting polymerisation of the said amine, the improvement comprising reducing the formation of the by-products without substantially reducing the formation of the amide by incorporating in the reaction mixture a reagent selected from reducing agents and the acids, and non-interfering salts thereof that are non-oxidising relative to the said oxidising agent, in an amount that results in reduction of by-product formation but substantially no reduction in formation of the amide.

2. A process according to claim 1 in which the reagent is an acid or non-intefering salt thereof.

3. A process according to claim 2 in which the copper catalyst is Raney copper.

4. A process according to claim 2 conducted by feeding the water, the catalyst, the oxidising agent, the reagent and the nitrile to a reaction vessel substantially continuously, removing the amide from the vessel substantially continuously, allowing the amount of catalyst in the vessel to increase significantly during the process, and then discharging the catalyst from the vessel.

5. A process according to claim 2 in which the said reagent is added substantially continuously or the said reagent is added whenever by-product formation is above a predetermined level.

6. A process according to claim 2 in which the catalyst is Raney copper, and the inhibitor comprises dissolved copper and the amount of the said reagent is insufficient to convert the black copper to pink, salmon or red copper.

7. A process according to claim 2 in which the nitrile is acrylonitrile or methacrylonitrile and the amide is acrylamide or methacrylamide.

8. A process according to claim 2 in which the hydrolysis is conducted at a temperature of above 100° C.

9. A process according to claim 1 in which the oxidising agent is nitrate.

10. A process according to claim 2 in which the said reagent is selected from non-polymerisable acidic buffers and non-interfering salts thereof.

11. A process according to claim 2 in which the said reagent is selected from saturated aliphatic organic acids having pKa1 of from 2 to 7, or a salt thereof.

12. A process according to claim 2 in which the said reagent is selected from acetic acid and copper acetate.

13. A process according to claim 2 in which the said reagent is only added for a short time and only when the by-product formation has increased undesirably.

14. A process according to claim 2 in which the catalyst that is introduced into the reaction mixture is a substantially black copper catalyst that has been washed with an aqueous solution of an acidic buffer that is a non-polymerisable organic acid or a salt thereof.

15. A process according to claim 14 in which the catalyst that is washed is selected from fresh Raney copper and catalyst that has become non-selective by use as the catalyst in a process for hydrolysing a nitrile to an amide in the presence of water and the catalyst, and mixtures of the said fresh and used catalysts.

16. A process for making an amide of formula $RCONH_2$ where R is ethylenically unsaturated hydrocarbon of 2 to 10 carbon atoms by hydrolysis of the corresponding nitrile RCN in a reaction mixture comprising water and a Raney copper catalyst, characterised in that the Raney catalyst is, before incorporation into the reaction mixture, washed with an aqueous solution of an acidic buffer that is a non-polymerisable organic acid.

17. A process according to claim 16 in which the buffer is a saturated aliphatic acid having pKa1 from 2 to 7 or a salt thereof.

18. A process according to claim 16 in which the catalyst is washed with aqueous acetic acid or copper acetate.

19. A process according to claim 2 in which the said reagent is selected from saturated aliphatic organic acids having pKa1 from 4 to 6.

20. A process according to claim 11 in which the said salt is with a weak base.

21. A process according to claim 11 in which the said salt is with copper, aluminum or sodium.

22. A process according to claim 14 in which the buffer is a saturated aliphatic acid having pKa1 from 2 to 7 or a salt thereof.

23. A process according to claim 2 in which the acidic buffer is acetic acid or copper acetate.

24. A process according to claim 16 in which the catalyst that is washed is selected from fresh Raney copper and catalyst that has become non-selective by use as the catalyst in a process for hydrolysing a nitrile to an amide in the presence of water and the catalyst, and mixtures of said fresh and used catalysts.

25. A process according to claim 17 in which the pKa1 is 4 to 6.

26. A process according to claim 1 in which the copper catalyst is Rainy copper, the oxidising agent comprises nitrate and the said reagent is a saturated aliphatic organic acid having pKa1 of from 2 to 7.

27. A process according to claim 26 in which the reagent is acetic acid or a salt thereof and is present in an amount of 300 to 600 ppm.

* * * * *